United States Patent
Sturman

[11] Patent Number: 5,215,525
[45] Date of Patent: Jun. 1, 1993

[54] SAFETY CASING FOR INTRAVENOUS CATHETER NEEDLE

[76] Inventor: Warren M. Sturman, 801 Ponce De Leon Dr., Ft. Lauderdale, Fla. 33316

[21] Appl. No.: 953,560

[22] Filed: Sep. 29, 1992

[51] Int. Cl.$^5$ .............................................. A61M 5/178
[52] U.S. Cl. ..................................... 604/164; 604/198
[58] Field of Search ............... 604/195, 198, 192, 263, 604/264, 164–170, 110

[56] References Cited

U.S. PATENT DOCUMENTS

| | | | |
|---|---|---|---|
| 3,595,230 | 7/1971 | Suyeoka et al. | 128/214.4 |
| 3,709,223 | 1/1973 | Macalalad et al. | 128/214.4 |
| 4,834,718 | 5/1989 | McDonald | 604/195 |
| 4,850,591 | 7/1989 | Wanderer et al. | 604/53 |
| 4,909,793 | 3/1990 | Vining et al. | 604/164 |
| 4,917,669 | 4/1990 | Bonaldo | 604/164 |
| 4,917,671 | 4/1990 | Chang | 604/168 |
| 4,944,725 | 7/1990 | McDonald | 604/164 |
| 4,944,728 | 7/1990 | Carrell et al. | 604/164 |
| 4,950,252 | 8/1990 | Luther et al. | 604/198 |
| 5,019,049 | 5/1991 | Haining | 604/165 |
| 5,026,351 | 6/1991 | Dizon | 604/264 X |
| 5,041,097 | 8/1991 | Johnson | 604/167 |
| 5,135,504 | 8/1992 | McLees | 604/164 |

*Primary Examiner*—John D. Yasko
*Attorney, Agent, or Firm*—Robert C. Kain, Jr.

[57] ABSTRACT

The safety casing for an intravenous catheter needle is used in conjunction with an elongated, hollow tube catheter having a catheter hub. The catheter hub has an interior catch rib therein. The safety casing includes an elongated needle case which is longer than the length of the needle. The case has a longitudinal slot therethrough. A movable slide control, attached to a proximal end of the needle, is disposed within the case and includes an operator tab protruding through the longitudinal slot. The needle case includes a distal end cap that is sized to fit within the proximal open end of the catheter hub. The end cap has a needle passage therethrough such that in all positions other than the fully retracted position, the needle is disposed within the needle passage. The end cap also includes a pair of needle jaws formed as flexible pincers within the needle passage. The pincers are biased towards the axial center line of the needle such that upon full retraction of the needle, by longitudinal movement of the slide control and operator tab through the slot of the needle casing, the pointed distal end of the needle moves axially inboard towards said needle case and both pincers snap towards the axial center line thereby effecting at least partial closure of the needle passage. This partial closure prohibits outboard longitudinal movement of the pointed distal end of the needle.

17 Claims, 6 Drawing Sheets

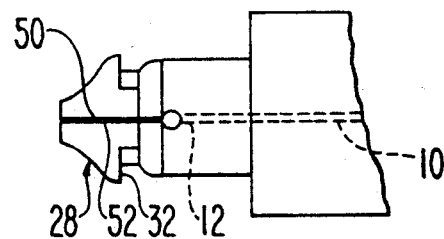
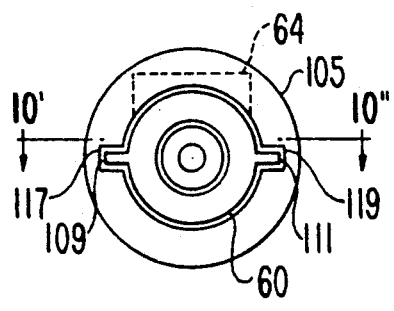
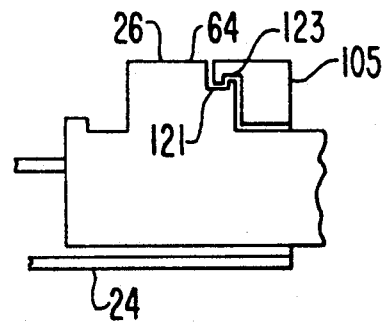
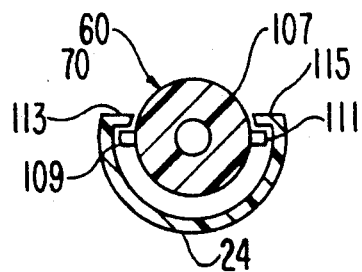
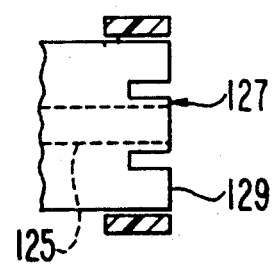
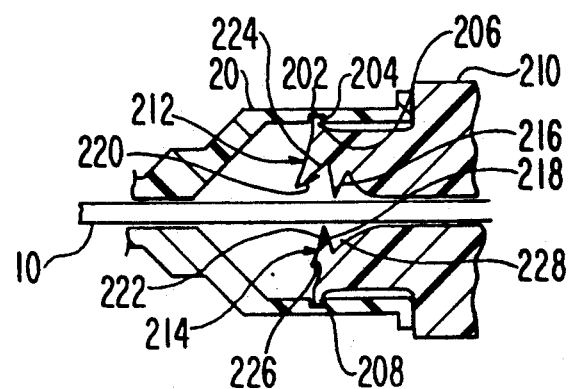

SAFETY CASING FOR INTRAVENOUS CATHETER NEEDLE

BACKGROUND OF THE INVENTION

The present invention relates to a safety casing for an intravenous catheter needle used in conjunction with a catheter and a catheter hub.

U.S. Pat. No. 4,834,718 to McDonald discloses a safety needle apparatus. The McDonald device includes a tab at the distal end of the needle casing which is biased upward by the needle passing from a tubular needle base through a needle passage in the needle casing and ultimately through the catheter. The tab, when biased upward by the needle passing through the needle passage, locks into a channel in the catheter hub. When the distal point end of the needle is withdrawn longitudinally and axially inboard beyond the tab, the tab flexes transversely, that is, towards the axial center line of the needle, thereby withdrawing from the channel in the catheter hub. In the McDonald device, the inboard flexed tab does not lock the pointed distal end of the needle within the needle casing.

U.S. Pat. No. 4,944,725 to McDonald discloses a safety needle apparatus. Dual tabs are biased above and below the needle and protrude inboard facing into catheter channels. When the pointed distal end of the needle is longitudinally withdrawn inboard into the needle casing, the tabs flex transversely, that is, towards the axial center line of the needle, and are withdrawn from the inboard channels of the catheter hub. Due to the withdrawal of the tabs from the catheter hub channels, the needle casing can be detached from the catheter hub. Again, this McDonald device does not lock the pointed distal end of the needle after withdrawal of the same longitudinally inboard away from the tab locks.

U.S. Pat. No. 4,944,728 to Carrell et al. discloses a one way rachet and flap system located at the proximal end of the needle. These flaps ratchet and lock with inboard protruding ledges on the needle casing. The distal pointed of the needle is not locked at the distal end of the casing but simply falls against a lip surface formed at the distal end of the needle casing. In another embodiment, the Carrell device utilizes a lever such that when the needle is fully withdrawn from the catheter and catheter hub, the proximal end of the needle moves into a keyway thereby moving the pointed distal end of the needle into a latch area. A flap then closes the latch area at the distal end of the needle casing.

U.S. Pat. No. 5,019,049 to Haining discloses an intravenous catheter and insertion device. Haining shows a notch lock at the proximal end of the needle carrier. The notch lock on the needle carrier cooperates with an inboard groove at the proximal end of the needle shield.

U.S. Pat. No. 4,950,252 to Luther et al. discloses a single hand actuated locking safety catheter. The proximal end of the needle is attached to a rectangular slide box that slides over a rectangular needle shield. When the needle is in the fully retracted position, transversely extending tabs on the proximal end of the needle shield lock within and mate with channels on the inboard side of the rectangular slide box.

U.S. Pat. No. 4,909,793 to Vining et al. discloses an intravenous catheter apparatus with a retractable stylet. Vining discloses a locking channel on the inboard side of the proximal end of a needle shield formed by symmetric bumps which cooperates with a ring attached to the distal end of a needle carrier such that upon full retraction of the needle, the ring is locked within the locking channel.

U.S. Pat. No. 3,595,230 to Suyeoka discloses an intravenous catheter placement unit with tubular guide sheath. The Suyeoka device includes a wing transversely protruding from a needle carrier which travels in a specially shaped cut-out or slot in the needle shield.

U.S. Pat. No. 4,850,961 to Wanderer et al. discloses indwelling placement device with guard. This device includes a tab at the proximal end of a needle carrier which travels in a cut-out slot of a needle shield. The tab, when the needle is fully retracted is moved into an enlarged housing in the needle shield at the proximal end of the shield thereby prohibiting outboard movement of the needle in needle carrier.

U.S. Pat. No. 4,917,671 to Chang discloses a flash plug for IV catheters. The flash plug permits one way air flow but blocks fluid or blood flow therethrough. U.S. Pat. No. 3,709,223 to Macalalad et al. discloses a sheath for a needle. U.S. Pat. No. 5,041,097 to Johnson discloses a protective end seal for an IV catheter fitting.

OBJECTS OF THE INVENTION

It is an objective of the present invention to provide a safety casing for a needle used in conjunction with an intravenous catheter.

It is a further object of the present invention to provide a safety casing which locks the pointed distal end of the needle upon full retraction of the needle inboard, longitudinally beyond the needle passage of an end cap of a needle case.

It is an additional object of the present invention to provide a latching mechanism on the end cap which, upon full retraction of the needle, closes a set of the needle jaws and transversely withdraws the lock tabs from complementary locking grooves on the inboard side of the catheter hub thereby detaching the needle case from the catheter hub.

It is a further object of the present invention to provide needle jaws having mating surfaces enabling complete closure of the needle passage through the end cap upon full retraction of the needle.

It is an additional object of the present invention to provide intermeshing needle jaws.

It is another object of the present invention to provide a needle case having two pair of needle jaws, a fore and an aft pair, which close upon full retraction of the needle from the needle passage of the end cap.

It is an additional object of the present invention to provide an end cap for a needle case which includes a pair of needle jaws at the needle passage through the end cap and a transversely formed means for latching the end cap and hence the needle case onto the catheter hub whereby, upon full retraction of the needle, the needle jaws close and unlatch the end cap and needle case from the catheter hub.

It is another object of the present invention to provide needle jaws which include pincers or needle teeth which extend longitudinally inboard toward the slide control such that upon full retraction of the pointed distal end of the needle beyond the needle jaws, the inboardly pointed pincers or teeth block longitudinal, outboard movement of the distal end of the needle into the needle passage in specially configured needle entrapment regions.

SUMMARY OF THE INVENTION

The safety casing for an intravenous catheter needle is used in conjunction with an elongated, hollow tube catheter having a catheter hub affixed to a proximal end of the hollow tube catheter. The catheter hub has an enlarged, proximal open end with an interior catch rib therein. The safety casing includes an elongated needle case which is longer than the length of the needle. The case has a longitudinal slot therethrough. A movable slide control is disposed within the case and includes an operator tab protruding through the longitudinal slot. The slide control is attached to a proximal end of the needle. The needle case includes a distal end cap. The outer surface of the end cap is sized to fit within the proximal open end of the catheter hub. The end cap has a needle passage therethrough such that in all positions other than the fully retracted position, the needle is disposed within the needle passage. The distal end cap also includes a transversely movable latch which cooperates with the interior catch rib on the inboard surface of the catheter hub. The end cap also includes a pair of needle jaws formed as flexible pincers within the needle passage. The pincers are biased towards the axial center line of the needle such that upon full retraction of the needle, by longitudinal movement of the slide control and operator tab through the slot of the needle casing, the pointed distal end of the needle moves axially inboard towards said needle case and both pincers snap towards the axial center line thereby effecting at least partial closure of the needle passage. This partial closure prohibits outboard longitudinal movement of the pointed distal end of the needle. Further enhancements include pincers having contact surfaces which mate and substantially close the needle passage upon full retraction of the needle, interlocking saw-tooth contact surfaces for the pincers, and pincers which point longitudinally inboard towards the slide control. Alternatively, certain spatial cavities are formed in the interior of the end cap by the closed or partially closed needle jaws, thereby prohibiting longitudinal outboard movement of the pointed distal end of the needle.

BRIEF DESCRIPTION OF DRAWINGS

Further objects and advantages of the present invention can be found in the detailed description of the preferred embodiments when taken in conjunction with the accompanying drawings in which:

FIG. 7 diagrammatically illustrates the outside of the end cap when the needle is fully retracted;

FIG. 8 diagrammatically illustrates a cross-sectional view of the slide control body and the needle case from the perspective of section line 8'—8" in FIG. 1;

FIG. 9A diagrammatically illustrates an end view of the needle case and slide control from the perspective of section line 9A'-9A" in FIG. 1;

FIG. 9B diagrammatically illustrates a rear latch lock for the slide control and the needle case;

FIG. 10 diagrammatically illustrates a cross-sectional view of the rear or proximal end surface of the needle case and slide control body from the perspective of section line 10'-10" in FIG. 9A;

FIG. 11 diagrammatically illustrates another embodiment of the needle jaws formed on the needle passage of the end cap, particularly illustrating the interlocking, intermeshing and complementary saw-tooth surfaces of the flexible pincers;

DETAILED DESCRIPTION OF THE PREFERRED EMBODIMENTS

The present invention relates to a safety casing for an intravenous (IV) catheter needle used in conjunction with an elongated, hollow tube catheter.

Figure 1:
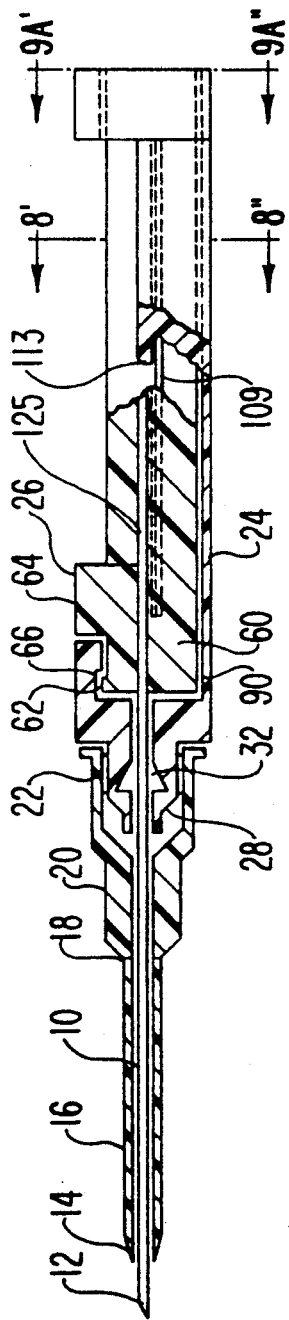
FIG. 1 diagrammatically illustrates a cross-sectional view of one embodiment of the safety casing wherein the needle is in a full forward position.

FIG. 1 diagrammatically illustrates a cross-sectional view of one embodiment of the needle, catheter, catheter hub and safety casing. Needle 10 has a pointed distal end 12 which protrudes beyond distal end 14 of catheter 16. The catheter is an elongated, hollow tube customarily made of plastic. The proximal end 18 of catheter 16 is affixed to a catheter hub 20. Catheter hub 20 includes an enlarged, proximal open end 22 that is best illustrated in FIG. 2.

Figure 2:
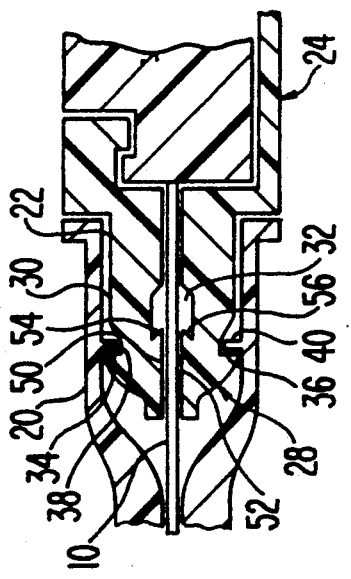
FIG. 2 diagrammatically illustrates the distal end of the needle case and catheter hub with the needle passing through the needle passage.

FIG. 2 diagrammatically illustrates an enlarged, cross-sectional view of catheter hub 20 and various other portions of the safety casing. The safety casing includes an elongated needle case 24 which is longer than the length of needle 10. See FIG. 1. A movable slide control 26 is movably disposed within needle case 24.

An end cap 28 is formed at the distal end of needle case 24. In this embodiment, the end cap performs two functions. The first function is to trap pointed distal end 12 of needle 10 within the body of needle case 24 upon full retraction of the needle. The second function of end cap 28 is to detach the needle case from catheter hub 20 upon full retraction of needle 10. In general, end cap 28 has an outer distal end surface 30 that has a complementary size and shape which fits within proximal open end 22 of catheter 20. Distal end cap 28 also includes a needle passage 32 therethrough such that needle 10 can slidably pass through the distal end cap. Outer surface 30 of end cap 28 includes at least one, and preferably a pair of ribs or flange latches 34 and 36 which cooperate with the distal surface portions of at least one, and preferably a pair of interior catch ribs 38 and 40 in hub 20. These catch ribs depend transversely or towards the axial center line of needle 10 into the interior space of catheter hub open end 22. As discussed later with respect to FIGS. 11 and 12, the interior catch ribs on the catheter hub may be channels, in which case the proximal surfaces of the channels operate as catch ribs.

End cap 28 also includes a pair of needle jaws 50 and 52 which are formed as flexible pincers within needle passage 32. These figures are diagrammatic but, in fact, the needle jaws closely grip the stem of needle 10. The transverse force applied by needle jaws 50, 52 does not prohibit the needle from moving longitudinally within needle passage 32.

Needle jaws 50, 52 more particularly include pincers which are biased towards the axial center line of the needle. These pincer teeth are shown in FIG. 2 as teeth 54 and 56.

In the preferred embodiment, slide control 26 (FIG. 1) includes a slide body 60. Slide body 60 includes a slide channel latch 62 near an operator tab 64. Needle case 24 includes a complementary casing channel latch 66. The slide channel latch and casing channel latch define a means for latching. The casing channel latch is complementary to slide channel latch 62 such that when both are transversely aligned and when needle 10 is in a full forward position, slide body 60 cannot be longitudinally moved in the absence of transverse force applied on operator tab 64 concurrent with longitudinal movement by the operator causing slide body 60 to move inboard within needle case 24. In a preferred embodiment, slide channel latch 62 and casing channel latch 66 are disposed near a longitudinal slot formed by needle case 24. Longitudinal slot 70 is best shown in FIG. 8 and is described later.

Figure 3:
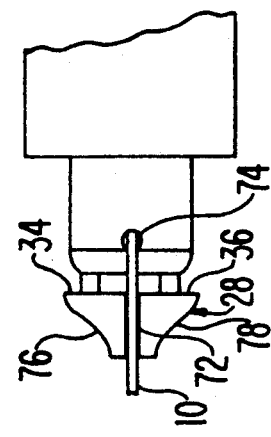
FIG. 3 diagrammatically illustrates the outer surface of the end cap for the needle casing.

FIG. 3 diagrammatically illustrates the outer contours of end cap 28. In this embodiment, end cap 28 has a distal end that is axially split and divided by keyway 72. A stress relief cut-out 74 permits upper and lower end portions 76 and 78 to flex when needle 10 resides within needle passage 32. Flange latches 34 and 36 are transversely biased away from the axial center line of needle 10 by the presence of the needle in needle passageway 32. As described above, latch flanges 34 and 36 cooperate with internally disposed catch ribs 38 and 40 on the interior of catheter hub 20.

Figure 4:
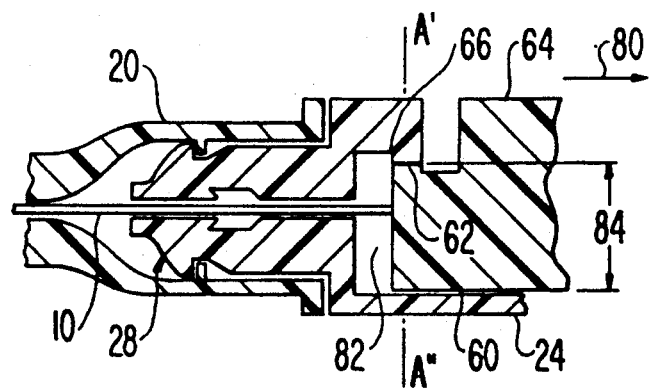
FIG. 4 diagrammatically illustrates a cross-sectional view of the end cap, the catheter hub, and the slide control when the slide control block latch has been uncoupled from the needle case latch.

FIG. 4 diagrammatically illustrates a cross-sectional view of catheter hub 20, needle 10, end cap 28, and portions of needle case 24 and slide body 60. In FIG. 4, the operator has transversely depressed operator tab 64 and has moved slide body 60 in the direction shown by arrow 80, that is, moving needle 10 longitudinally inboard towards the proximal end of needle case 24. Needle case 24 defines a slide track 82 therein which has a transverse, cross-sectional height dimension 84 slightly greater than the cross-sectional height dimension of slide body 60 plus a depth of the shallower one of slide channel latch 62 or casing channel latch 66. As shown in FIG. 1, when slide channel latch 62 is latched with casing channel latch 66, there is an interspace 90 between the lower portions of slide body 60 and the inboard surface of needle case 24. This permits the operator to transversely depress operator tab 64 and move needle 10 longitudinally inboard into needle case 24 such that latches 62 and 66 become uncoupled. The critical dimension is the cross-sectional height of slide channel dimension 84 coplanar with the locked channel latches generally along plane A'-A" in FIG. 4.

Figure 5:
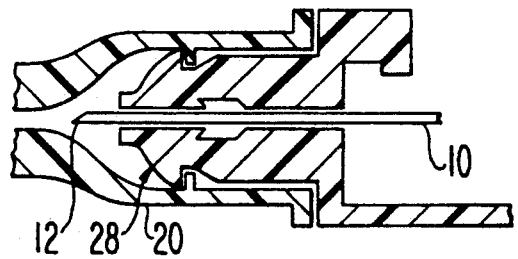
FIG. 5 diagrammatically illustrates a cross-sectional view of the end cap, catheter hub when the pointed distal end of the needle is slightly forward of the needle passage.

FIG. 5 diagrammatically illustrates the safety casing immediately before pointed distal end 12 of needle 10 is withdrawn from the needle passage of end cap 28.

Figure 6:
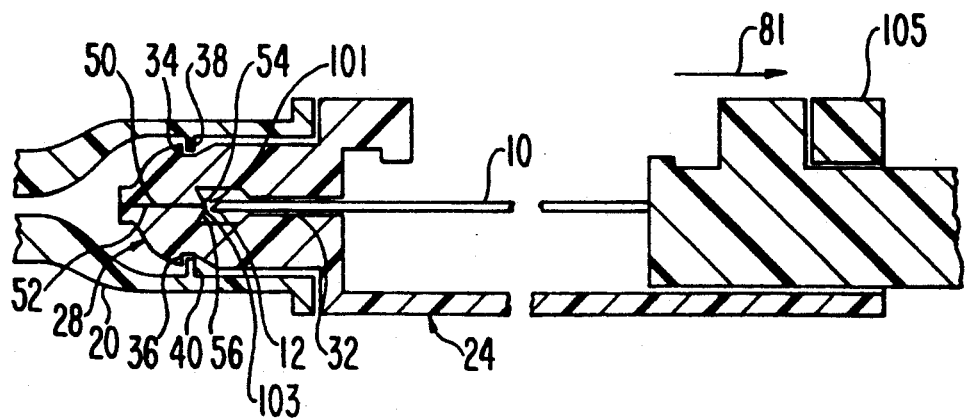
FIG. 6 diagrammatically illustrates a cross-sectional view of the end cap, catheter hub and the stop control for the slide when the pointed distal end of the needle is in a fully retracted position.

FIG. 6 diagrammatically illustrates needle 10 in a fully retracted position. Pointed distal end 12 of needle 10 has been longitudinally removed from needle passage 32 such that needle jaws 50, 52 and particularly flexible pincers 54, 56 have snapped towards the axial center line of needle 10. An important feature of the present invention is at least the partial closure of the distal portion of needle passage 32. In the illustrated embodiment, needle passage 32 has been completely substantially closed by the mating of contact surfaces of each pincer. In the fully retracted position, pointed distal end 12 of needle 10 cannot be moved, either deliberately or accidentally, longitudinally forward or outboard of needle casing 24. Pincer teeth 54, 56 form an inboard pointing, arrowhead shape when the respective contact surface mate. Also, upper and lower forward pointing, arrowhead shaped needle entrapment regions 101 and 103 are formed in the mid-region of needle passage 32. These needle entrapment regions entrap the pointed distal end 12 of needle 10 and provide a safety feature such that even if the distal forward region of needle passage 32 is not fully closed, the distal pointed end 12 of needle 10 will be trapped by these forward pointing, arrowhead shaped entrapment regions 101, 103.

Since the distal surface portion of end cap 28 is biased transversely outward due to the presence of the body of needle 10 in the needle passage, when the pointed distal end 12 is removed from the needle passage, the distal surface portion of end cap 28 moves transversely and closes the distal portion of needle passage 32. This transverse movement unlatches latch flanges 34 and 36 from catheter ribs 38 and 40. Accordingly, needle casing 24 is unlatched or uncoupled from catheter hub 20.

Needle case 24 also includes a rear or proximal end stop 105 that blocks further longitudinal movement in direction 81 of slide body 60.

FIG. 7 diagrammatically illustrates the outer portion of end cap 28 when pointed distal end 12 of needle 10 is fully retracted beyond the distal region of needle passage 32. The closure of needle jaws 50 and 52 is illustrated in FIG. 7.

FIG. 8 diagrammatically illustrates a cross-sectional view of needle case 24 and the mid-region section 107 of slide body 60 from the perspective of section line 8'-8Δ in FIG. 1. In the illustrated embodiment, slide body 60 is generally cylindrical in shape. However, a square or rectangular shape would work equally well. Slide body 60 includes radially outboard extending body ribs 109, 111. These ribs provide entrapment of slide body 60 within needle case 24 due to a pair of facing, longitudinal case lips 113, 115. Of course, a specifically defined track could be provided by two pair of case lips, each pair defining a certain track for body ribs 109, 111. Body rib 109 and case lip 113 are illustrated in the partial broken away view in FIG. 1.

FIG. 9A diagrammatically illustrates an end view of the safety casing from the perspective of section line 9A'-9A" in FIG. 1. Case end stop 105 limits further longitudinal outboard movement of slide body 60 due to operator tab 64. Body ribs 109, 111 slide longitudinally outboard of case end stop 105 due to case end cut-outs 117 and 119.

As an additional safety feature, FIG. 9B shows a rear end latch configuration between case end stop 105 and the proximal end surface of slide control 26. Particularly, the proximal end surface of operator tab 64 may include a tab channel latch 121 which locks within end stop channel latch 123 upon full retraction of the needle case 24.

Since it is sometimes appropriate to withdraw a minimal amount of blood or body fluid after insertion of the needle in the vein, slide body 60 may include a longitudinal fluid passage 125 (see FIG. 1) therethrough. Fluid passage 125 is in fluid communication with the lumen of needle 10. In order to gather or contain this blood or body fluid, slide body 60 includes a fluid communication port interface 127 (FIG. 10) at its rear or distal end body surface 129. Standard blood or fluid collection devices can be coupled to interface 127.

Figure 12:
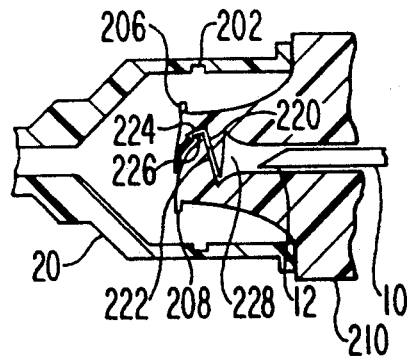
FIG. 12 diagrammatically illustrates the interlocked saw-tooth pincers after the pointed distal end of the needle is a fully retracted position.

FIGS. 11 and 12 diagrammatically illustrate a different embodiment of the needle jaws formed as flexible pincers. Catheter hub 20 includes an interior catch rib that is formed as an interior hub channel 202 on the inboard surface of the hub. The proximal channel wall 204 acts as an interior catch rib for end cap latch flanges 206 and 208.

Distal end cap 210 includes a pair of needle jaws 212 and 214 which have flexible pincers 216, 218 with contact surfaces 220, 222 formed as intermeshing, complementary, saw-tooth surfaces. Included in the saw-tooth surfaces are latch locks 224 and 226 that lock needle jaws 212, 214 together when needle 10 is fully withdrawn from needle passageway 228.

FIG. 12 diagrammatically illustrates the locked and intermeshed saw-tooth surfaces 220, 222 when the pointed distal end 12 of needle 10 has been fully withdrawn from the distal portion of needle passage 228. Latch locks 224, 228 snap together and lock the intermeshed, saw-tooth surfaces.

FIG. 12 also shows the transverse retraction of latch flanges 206 and 208 from hub channel 202. Since the interior of catheter hub 20 defines a circular cavity, hub channel 202 is a circumferential internal channel. The transverse retraction of latch flanges 206, 208 permits the uncoupling end cap 210 from catheter hub 20.

Figure 13:
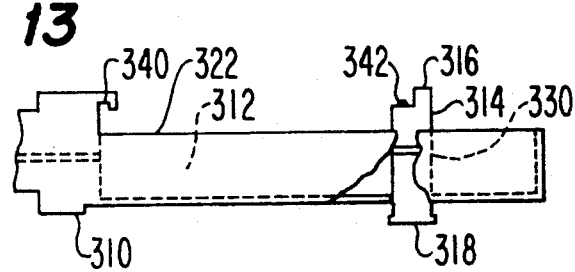
FIG. 13 diagrammatically illustrates another embodiment of the slide control having upper and lower operator tabs on the slide control body.
Figure 16:
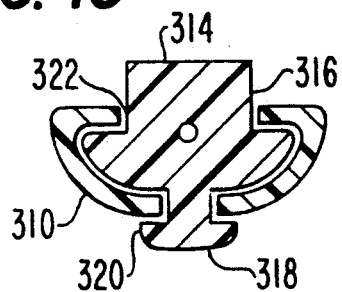
FIG. 16 diagrammatically illustrates a cross-sectional view of the slide control body with dual operator tabs as shown in the embodiment of FIG. 13.

FIG. 13 shows an alternate embodiment of the slide body. Needle case 310 defines a slide track 312 within which slides slide body 314. Slide body 314 includes upper operator tab 316 and lower operator tab 318. FIG. 16 shows lower operator tab 318 protruding through a lower longitudinal slot 320 in needle case 310. The upper longitudinal slot 322 is defined by needle case 310. Also in FIG. 13, slide body 316 does not have an elongated shape but is truncated essentially at proximal end 330.

Case channel latch 340 is defined by the needle case near the distal end of upper longitudinal slot 322. Case channel latch 340 cooperates with latch 342 provided on the distal side of operator tab 316.

Figure 14:
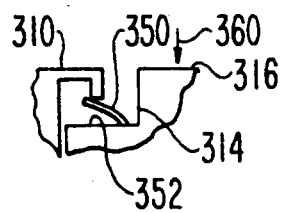
FIGS. 14 and 15 diagrammatically illustrate casing channel latch and side channel latches to lock the slide control body on the needle case when the needle is in the full forward position.
Figure 15:
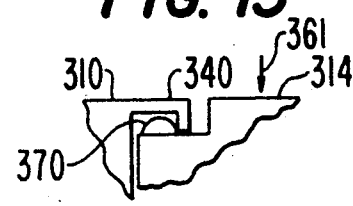

FIGS. 14 and 15 diagrammatically illustrate two types of latches. In FIG. 14, slide body latch 342 is configured as a flexible arm 350 riding atop a ridge 352. Upon depression of operator tab 316 in the direction shown by arrow 360, slide control 314 is uncoupled from needle case 310. In FIG. 15, case latch 340 cooperates with ridge 370 defined at the distal end of slide body 314 near upper longitudinal slot 322. Upon transverse movement by the operator in the direction of arrow 361, slide control 314 is uncoupled from needle case 310.

Figure 17:
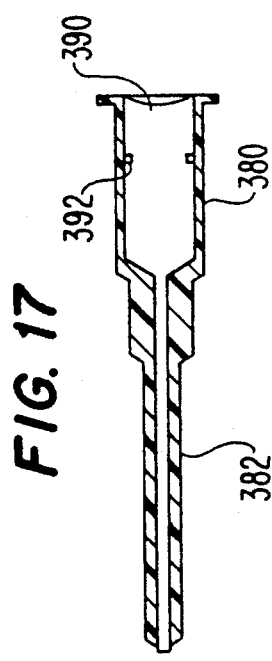
FIG. 17 diagrammatically illustrates an elongated, hollow tube catheter in a catheter hub.

FIG. 17 diagrammatically illustrates a cross-sectional view of catheter hub 380 which is at the proximal end of catheter 382. Catheter hub 380 includes an enlarged proximal open end 390 and an interior catch rib 392.

Figure 18:
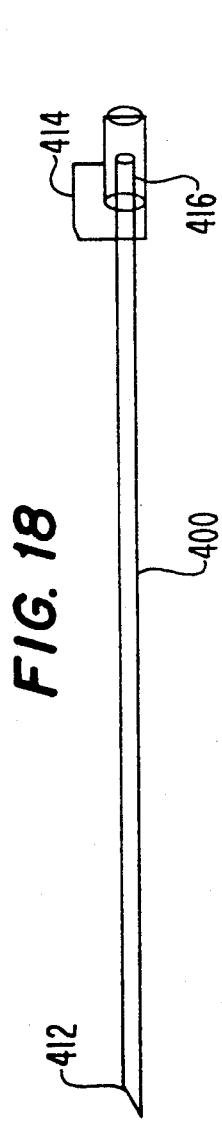
FIG. 18 diagrammatically illustrates an elongated needle having a slide control disposed on a proximal end of the needle.
Figure 19:
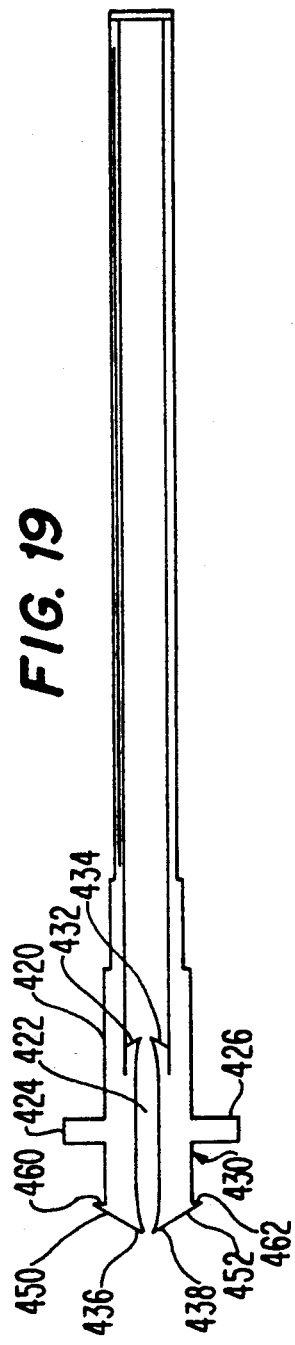
FIG. 19 diagrammatically illustrates an alternative embodiment of the needle case having two pair of needle jaws, one pair facing longitudinally inboard towards the interior of the needle case and the other pair facing towards the catheter hub.

FIG. 18 illustrates needle 400 having a pointed distal end 412 and a slide body control 414 attached to the proximal end 416 of needle 400. FIG. 19 illustrates needle casing 420. Needle channel 422 is provided at the distal end of needle case 420. Upper and lower operator tabs 424 and 426 are provided on the end cap such that the operator can transversely compress tabs 424 and 426. Needle case 420 also includes a distal end cap 430. The distal end cap includes needle jaws 432 and 434 which form rearward or inboard facing pincers about needle passage 422. A forward or distal pair of pincers 436 and 438 are also formed about needle passage 422. In order to latch needle case 420 on catheter hub 380, the means for latching is formed as flexible, forward depending arms 450 and 452. Arms 450, 452 extend from end cap 430. Arms 450 and 452 include latch surfaces 460 and 462. Latch surfaces 460, 462 cooperate with catheter rib 392 shown in FIG. 17.

Figure 20:
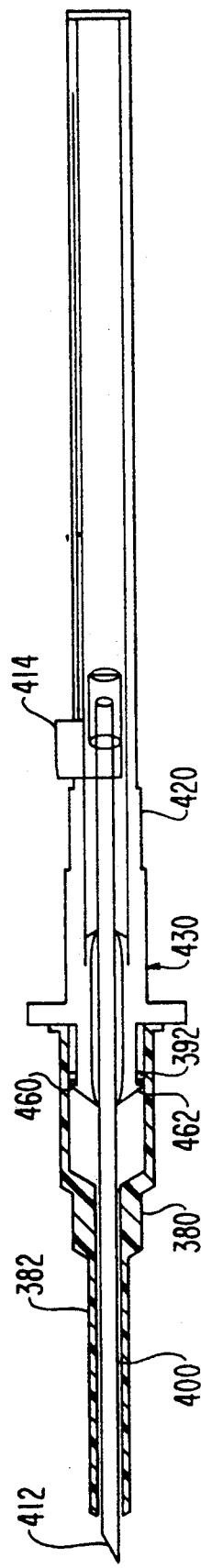
FIG. 20 diagrammatically illustrates the catheter, catheter hub, a needle in a full forward position, and the two pair of needle jaws in the distal end cap of the needle case.

In FIG. 20, needle 400 is disposed within catheter 382 and catheter hub 380, and needle case 420 has been removably attached to hub 380 due to the latching action of latch ledges 460 and 462 on hub rib 392. Slide control 414 is in a full forward position such that the pointed distal end 412 of needle 400 protrudes from the distal end of catheter 382.

Figure 21:
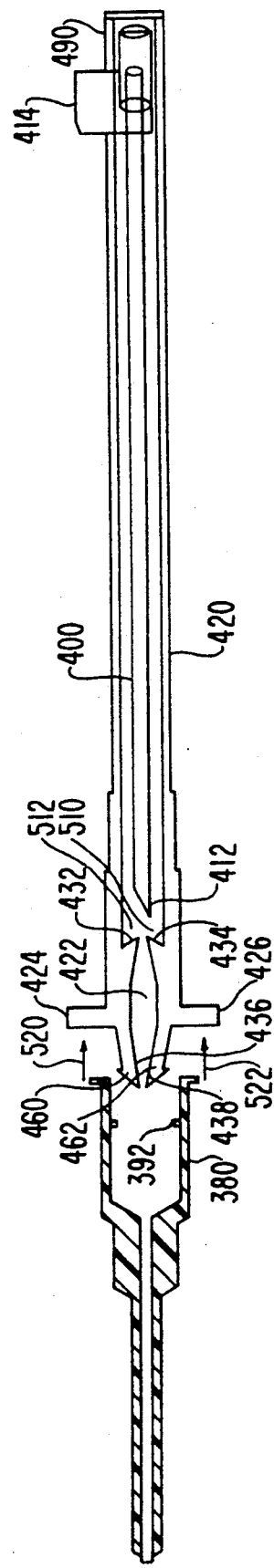
FIG. 21 diagrammatically illustrates the detached catheter hub and needle case having two pair of needle jaws when the needle is in a fully retracted position.

In FIG. 21, the pointed distal end 412 of needle 400 is in a fully retracted position such that slide control 414 is positioned near rear stop 490 of needle case 420. Rearward pincer jaws 432 and 434 have snapped to partially close needle passage 422 and provide upper and lower forward pointing, arrowhead shaped needle entrapment areas 510 and 512. The other pair of needle jaw pincers 436 and 438 also partially close needle passage 422. Due to the transverse compression of operator tabs 424 and 426, latches 460 and 462 have been uncoupled from internal rib 392. The operator has moved needle case 420 away from catheter hub 380 as shown by arrows 520 and 522.

Although the present invention has been illustrated as having at least one pair of needle jaws formed as flexible pincers, the needle jaws can be configured in a set of three, four or other multiples sufficient to at least partially close the needle passage upon full retraction of the pointed distal end of the needle. In additional to partial closure of the needle passage, it is important that the needle jaw pincers form needle entrapment areas such that if the pointed distal end of the needle is accidentally or deliberately moved longitudinally forward, the specially configured entrapment areas entrap or capture the pointed end of the needle, thereby prohibiting further forward movement of the needle. Also, the concurrent uncoupling of the needle case from the catheter hub is an important feature of the present invention. When the needle case is uncoupled or unlatched from the catheter hub, it is unlikely that the operator would attempt to re-insert the needle through the catheter.

The claims appended hereto are meant to cover modifications and changes within the spirit and scope of the present invention.

What is claimed is:

1. A safety casing for an intravenous catheter needle used in conjunction with an elongated, hollow tube catheter having a catheter hub affixed to a proximal end of said hollow tube catheter, said hub having an enlarged, proximal open end with an interior catch rib therein, said needle adapted to travel within said catheter and such that a pointed distal end of said needle protrudes from a distal end of said catheter when said needle is in a full forward position, said safety casing comprising:
   an elongated needle case longer than said needle, said case having a longitudinal slot therein;
   a movable slide control disposed within said case and having a operator tab protruding through said longitudinal slot, said slide control attached to a proximal end of said needle;
   a distal end cap formed at a distal end of said needle case, an outer distal end surface of said end cap having a complementary size and shape to fit within said proximal open end of said catheter hub, said end cap having needle passage therethrough;
   transversely movable means for latching a distal portion of said interior catch rib of said catheter hub, said means for latching disposed on said end surface of said end cap; and
   a pair of needle jaws formed as flexible pincers within said needle passage of said end cap, said pincers being biased towards an axial center line of said needle such that upon full retraction of said needle by longitudinal movement of said slide control via said operator tab through said slot, the pointed distal end of said needle moves inboard said needle case and both pincers snap towards said axial center line thereby effecting at least partial closure of said needle passage with respect to said needle and prohibiting longitudinal, outboard movement of said pointed distal end of said needle.

2. A safety casing as claimed in claim 1 wherein each pincer has a respective contact surface for the other pincer such that upon full retraction of said needle, said contract surfaces mate and substantially close said needle passage.

3. A safety casing as claimed in claim 2 wherein said contact surfaces are formed as intermeshing, complementary, saw toothed surfaces.

4. A safety casing as claimed in claim 2 wherein said pincers form an inboard pointing arrowhead shape when said contract surfaces mate.

5. A safety casing as claimed in claim 2 wherein said means for latching is formed as a transverse counterpart of said pair of needle jaws such that when said needle is in all positions other than the fully retracted position, said needle separates said pincers of said jaws and forces said transversely movable means for latching towards said distal portion of said interior catch rib of said catheter hub and such that upon full retraction of said needle, said pincers close said needle passage and said means for latching moves transversely towards said axial centerline thereby unlocking said needle case from said catheter hub.

6. A safety casing as claimed in claim 5 wherein said slide control includes a slide channel latch near said operator tab, said needle case includes a complementary casing channel latch on a proximal end surface of said end cap, said slide channel latch adapted to be detachably locked with said casing channel latch when said needle is in said full forward position.

7. A safety casing as claimed in claim 6 wherein said casing channel latch and said slide channel latch are disposed near said slot, said needle case defining a slide track within which travels a slide body portion of said slide control, said slide track having a cross-sectional dimension, co-planar with the locked channel latches, slightly larger than the cross-sectional dimension of said slide body portion plus a depth of the shallower one of said latch channels.

8. A safety casing as claimed in claim 6 wherein said needle case includes a pair of facing longitudinal lips on opposing sides of said slot, and said slide control has a slide body portion which is captured by said opposing lips within a slide track defined by said needle case.

9. A safety casing as claimed in claim 5 wherein said interior catheter rib defines a transverse ledge and said means for latching co-acts with said transverse ledge to detachably lock said end cap and needle case to said catheter hub.

10. A safety casing as claimed in claim 1 wherein said slide control includes a slide body portion, said slide body having an longitudinal fluid passage therethrough in fluid communication with a lumen of said needle.

11. A safety casing as claimed in claim 10 wherein said slide body forms a fluid communication port interface on a rear end thereof.

12. A safety casing as claimed in claim 11 wherein said needle case includes a stop prohibiting further retractive movement of said needle such that said pointed distal end of said needle does not move longitudinal inboard significantly away from said needle jaws.

13. A safety casing as claimed in claim 1 wherein said means for latching is formed as flexible, forward depending arms extending from said end cap and into said open end of said hub, said means for latching having transversely protruding operator tabs protruding from said arms and beyond said end cap such that upon compression of said operator tabs, said means for latching transversely moves away from said distal portion of said interior catch ribs in said catheter hub.

14. A safety casing as claimed in claim 1 wherein said pincers, when said needle is fully retracted, form upper and lower, forward pointing, arrowhead shaped, needle entrapment regions about said axial centerline of said needle.

15. A safety casing as claimed in claim 1 including two pair of needle jaws, one pair of jaws having pincers facing inboard toward the slide control and the other pair of jaws having pincers facing outboard away from said needle case.

16. A safety casing as claimed in claim 15 wherein said other pair of jaws includes said means for latching formed as a transverse counterpart of said other pair of jaws.

17. A safety casing as claimed in claim 1 wherein said pair of needle jaws has pincers which point longitudinally inboard toward said slide control.

* * * * *